United States Patent [19]

Boaz

[11] Patent Number: 5,306,638
[45] Date of Patent: Apr. 26, 1994

[54] AMINE ADDITIVE ASSISTED ENZYMATIC ESTERIFICATION OF 1,2-DIOL MONOSULFONATES

[75] Inventor: Neil W. Boaz, Waterloo, N.Y.

[73] Assignee: Eastman Kodak Company, Rochester, N.Y.

[21] Appl. No.: 854,944

[22] Filed: Mar. 20, 1992

[51] Int. Cl.$^5$ .................... C12P 41/00; C12P 11/00
[52] U.S. Cl. ................................ 435/280; 435/130; 435/874; 435/876
[58] Field of Search ...................... 435/280, 130

[56] References Cited

U.S. PATENT DOCUMENTS

| | | | |
|---|---|---|---|
| 4,745,066 | 5/1988 | Hamaguchi et al. | 435/280 |
| 4,996,158 | 2/1991 | Oda et al. | 435/280 |
| 5,032,523 | 7/1991 | Amano et al. | 435/280 |

FOREIGN PATENT DOCUMENTS

| | | | |
|---|---|---|---|
| 0197484 | 10/1986 | European Pat. Off. | |
| 290662 | 6/1991 | German Democratic Rep. | |
| 62-158250 | 12/1985 | Japan | |
| 62-209049 | 10/1986 | Japan | C12P 11/00 |

OTHER PUBLICATIONS

Bilyk A, JAOCS 68:320-23 (1991).
Steglich W, Agnew Chem 81:1001 (69).
Klibanov, A. M., "Asymmetric Transformations Catalyzed by Enzymes in Organic Solvents", *Acc. Chem. Res.*, 23: 114–120 (1990).
Kirchner, G. et al; "Resolution of Racemic Mixtures via Lipase Catalysis in Organic Solvents", *J. Am. Chem. Soc.*, 107, 1983, 7072–7076.
Degueil–Castaing, M. et al; "Enzymatic Reactions in Organic Synthesis: 2-Ester Interchange of Vinyl Esters", *Tetrahedron Lett.* 28, 1987, 953.
Chen, C.-S. et al; "Quantitative Analyses of Biochemical Kinetic Resolutions of Enantiomers", *J. Am. Chem. Soc.*, 104, 1982, 7294–7299.
Chen, C.-S. et al; "A Convenient Chemoenzymatic Synthesis of (R)- and (S)-(Chloromethyl)oxirane", *J. Chem. Soc. Perkin Trans.*, I, 1990, 2559–2561.
Chen, C.-S. et al; "A Chemoenzymatic Access to Optically Active 1,2-Epoxides", *Tetrahedron Lett.*, 30, 1989, 7165–7168.
Hamaguchi, S. et al; "Lipase–catalyzed Stereoselective Hydrolysis of 2–Acyl and 1–p–Tolylsulfonyl Substituted Propanediol and Butanediol" *Agric. Biol. Chem.*, 50(6), 1986, 1629–1632.
Theil, F. et al, "Investigation of the Pancreatin-Catalyzed Acylation of cis–Cyclopent–2–ene–1,4–diol with Various Trichloroethyl and Vinyl Alkanoates," *Liebigs Ann. Chem.*, 1991, 195–200.

(List continued on next page.)

*Primary Examiner*—Douglas W. Robinson
*Assistant Examiner*—S. Saucier
*Attorney, Agent, or Firm*—Judith A. Roesler; J. Jeffrey Hawley

[57] ABSTRACT

A process has been developed for the enzymatic esterification of 1,2-diol monosulfonates comprising contacting an ester; a 1,2-diol monosulfonate; an enzyme derived from a microorganism or animal organ which has stereoselective activity to asymmetrically esterify said 1,2-diol monosulfonate; in the presence of a nonhydroxylic organic solvent and an amine additive of the general formula $R^3{}_2R^4N$, wherein $R^3$ may be the same or different and is selected from hydrogen or a straight or branched $C_1$–$C_{20}$ alkyl; and $R^4$ is a straight or branched $C_1$–$C_{20}$ alkyl; or an unsubstituted or substituted $C_3$–$C_{20}$ aryl or heteroaryl group (with saisd substituent selected from $C_1$–$C_4$ alkyl, halogen, or $C_1$–$C_4$ alkoxy, and said hetero atom selected from nitrogen, sulfur, or oxygen);

to produce a mixture of enantiomerically enriched unreacted 1,2-diol monosulfonate and the corresponding antipodal enantiomerically enriched ester. The resulting enantiomerically enriched products are useful chemical intermediates that may be employed in the synthesis of pharmaceutical and agricultural chemicals.

12 Claims, 1 Drawing Sheet

OTHER PUBLICATIONS

Theil, F., et al, "Synthesis of (1S,4R)-(−)-4-Hydroxy-2-cyclopentenyl Acetate by a Highly Enantioselective Enzyme-Catalyzed Transesterification in Organic Solvents," *Synthesis,* 1988, 540–541.

Jommi, G. et al, "Enantioselective Synthesis of 3(S)-Acetoxy-5(R)-Hydroxycylopent-1-ene by Enzymatic Transesterification in Organic Solvents," *Gazzetta Chimica Italiana,* 118, 1988, 863–864.

Crawford, R. et al, "The thermally induced rearrangements of 2-vinyloxirane," *Can. J. Chem.,* 54, 1976, 3364–76.

CA 112:177061c, vol. 112, 1990, p. 595, "Optical resolution of racemic alcohols with hydrolase", JP 01-235,599.

AMINE ADDITIVE ASSISTED ENZYMATIC ESTERIFICATION OF 1,2-DIOL MONOSULFONATES

FIELD OF THE INVENTION

This invention relates to the preparation of a mixture of enantiomerically enriched 1,2-diol monosulfonates and the corresponding enantiomerically enriched antipodal esters by additive assisted enzymatic esterification of 1,2-diol monosulfonates. The resulting enantiomerically enriched products and their derivatives are useful chemical intermediates that may be employed in the synthesis of many enantiomerically enriched compounds including pharmaceuticals and agricultural chemicals.

BACKGROUND OF THE INVENTION

Chemoenzymatic synthesis employs both chemical and biocatalytic steps in a reaction sequence. The biocatalytic transformations convert one organic compound to another by use of enzymes, either isolated or as part of biological systems.

Enzymes derived from biological systems (for example, from a microorganism or an animal organ) have been particularly useful in the resolution of racemic compounds. In these systems, a chiral compound composed of two enantiomers is used as the substrate for the enzyme. The enzyme specifically recognizes and favors only one of the enantiomers as the substrate for the enzymatic reaction. The stereospecificity of the enzyme optimally affords a product mixture having a 50% conversion to a single enantiomer product and 50% recovered starting material of opposite configuration.

The product mixture can be analyzed for enantioselectivity by numerous methods. The optical purity of the products defines the degree of enantioselectivity of an enzymatic resolution and can be expressed as the "E" value, a directly proportional measure of the R to S reactivity rate ratio. Because the "E" value is independent of conversion, it is particularly useful in evaluating kinetic resolutions, as described in Chen, C. S, et al, *J. A Chem. Soc.* 1982, 104, p. 7249. These "E" values are determined by the optical purity of both the product and recovered starting material, with higher optical purities affording higher "E" values.

For present purposes, an "enantiomerically enriched" compound is defined as having an enantiomeric excess ("ee") of greater than about 80%±2%. The enantiomerically enriched product is desirable because it can be further converted into various enantiomerically enriched compounds. For example, single enantiomeric compounds are useful in the synthesis of pharmaceutical compounds where one enantiomeric form of the compound may be pharmaceutically active and the other enantiomeric form may be inactive or even detrimental.

There are many different methods that are used, including biocatalysis, to prepare enantiomerically enriched compounds. Hydrolase enzymes have been employed with success for the stereospecific preparations of alcohols and esters using several reaction variants. The conventional enzymatic hydrolysis reaction is normally performed in aqueous media with pH control and entails hydrolysis of a chiral ester substrate to afford the corresponding acid and alcohol products. Enzymatic transesterification commonly also refers to the use of a chiral ester substrate, but the products are a second ester and the alcohol portion of the substrate from the reaction of the acylated enzyme with an alcohol rather than water. The enzymatic esterification of a chiral substrate alcohol is quite different, being a synthetic rather than a hydrolytic process with respect to the substrate.

The enzymatic esterification of an alcohol derivative in an organic solvent relies on the absence of water to reverse an equilibrium which normally favors ester hydrolysis rather than synthesis, as diagramed in the reaction sequence shown below. An achiral acyl donor acylates the enzyme in the first step (I). In the second step (II) the acyl-enzyme reacts with the desired chiral substrate alcohol to form a corresponding enantiomerically enriched product ester, an unreacted enantiomerically enriched alcohol of the opposite configuration, and free enzyme.

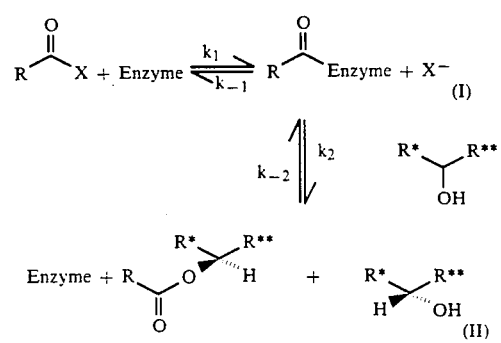

The choice of the X radical of the acyl donor is significant in assisting the equilibrium reversal of the reaction. If the X radical is a simple alcohol, the radical can concrete favorably with the desired alcohol for the acyl-enzyme complex ($k_{-1}k_2$) and thus slow the desired reaction immensely. To improve the reaction rate, either the nucleophilicity of the alcohol released upon enzyme acylation can be reduced or else the first step of the reaction can be made irreversible. For example, vinyl esters are preferred as acyl donors because the alcohol portion, upon release from the ester, completely isomerizes to the corresponding aldehyde, effectively shutting down $k_{-1}$.

In many cases, the enzymatic esterification reaction of a chiral substrate has been found to offer significant operational advantages over the corresponding enzymatic hydrolysis. Besides being a step shorter (the preparation of the racemic ester is unnecessary), pH control of the reaction mixture is avoided. In the enzymatic esterification, filtration to remove the enzyme followed by solvent removal affords the products in nearly quantitative yield without requiring the extractive isolation procedure usually necessary in the enzymatic hydrolysis reaction. Further, reuse of the enzyme is possible in the enzymatic esterification, whereas in the hydrolysis reaction this is usually not the practice.

The enzymatic hydrolysis and alcoholysis of esters of 1,2-diol monotosylates is known. Unfortunately, the enzymatic esterification of 1,2-diol monotosylates under standard conditions, though reported, can suffer from severe complications. This is exemplified by the attempted enzymatic esterification of 1-tosyloxy-2-hydroxy-3-butene. The first significant problem is that the enzymatic esterification of this species often stops short of the optimal 50% conversion rate. In extreme cases, little conversion to products is observed at all. Only upon repeated addition of more enzyme does the reaction eventually reach 50% conversion. Further, the reaction products show only moderate enantiomeric excess. Improvement of the enzymatic esterification rate and percent conversion percentage as well as improvement of the enantiospecificity is necessary before enzymatic esterification of 1,2-diol monosulfonates is suitable for commercial scale.

SUMMARY OF THE INVENTION

In accordance with the present invention, there is provided a process for the enzymatic esterification of 1,2-diol monosulfonates comprising contacting:

(a) an ester having a general formula:

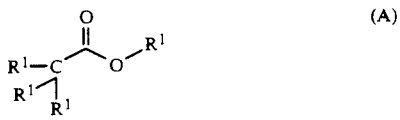

wherein:

$R^1$ may be the same or different and is defined as hydrogen, halogen, a straight or branched $C_1$–$C_{10}$ alkyl or $C_2$–$C_{10}$ alkenyl group, a straight or branched $C_1$–$C_6$ ether, a straight or branched $C_1$–$C_6$ thioether, or a tertiary dialkylamino having alkyl groups with 1 to 6 carbon atoms with each alkyl the same or different;

(b) a 1,2-diol monosulfonate having the formula:

wherein:

$R^2$ is a straight or branched, substituted or unsubstituted $C_1$–$C_{10}$ alkyl group, a straight or branched, substituted or unsubstituted $C_2$–$C_{10}$ alkenyl group, or a straight or branched, substituted or unsubstituted $C_2$–$C_{10}$ alkynyl group, with the substituents designated above selected from halogen, cyano, $C_1$–$C_5$ alkoxy or $C_1$–$C_5$ alkylthio, and Ar represents a substituted or unsubstituted $C_4$–$C_{10}$ aromatic or heteroaromatic group with substituents selected from halogen atoms, nitro, or a dialkylamino having alkyl groups with 1 to 3 carbon atoms with each alkyl the same or different;

(c) a microorganism or animal organ-derived enzyme having stereoselective activity to asymmetrically esterify said 1,2-diol monosulfonate;

(d) a nonhydroxylic organic solvent; and (e) an amine additive of the general formula $R^3{}_2R^4N$, wherein $R^3$ may be the same or different and is selected from hydrogen or a straight or branched $C_1$–$C_{20}$ alkyl, and $R^4$ is a straight or branched $C_1$–$C_{20}$ alkyl; or an unsubstituted or substituted $C_3$–$C_{20}$ aryl or heteroaryl group (with said substituent selected from $C_1$–$C_4$ alkyl, halogen, or $C_1$–$C_4$ alkoxy, and said heteroatom is selected from nitrogen, sulfur, or oxygen), to produce a mixture of enantiomerically enriched 1,2-diol monosulfonate and the corresponding enantiomerically enriched antipodal ester.

The invention is particularly advantageous because it provides an enhanced enzymatic conversion rate with no sequential enzyme addition necessary. A further advantage of this invention is the enhanced enantioselectivity demonstrated by the reaction products.

DETAILED DESCRIPTION OF THE INVENTION

Figure 1:
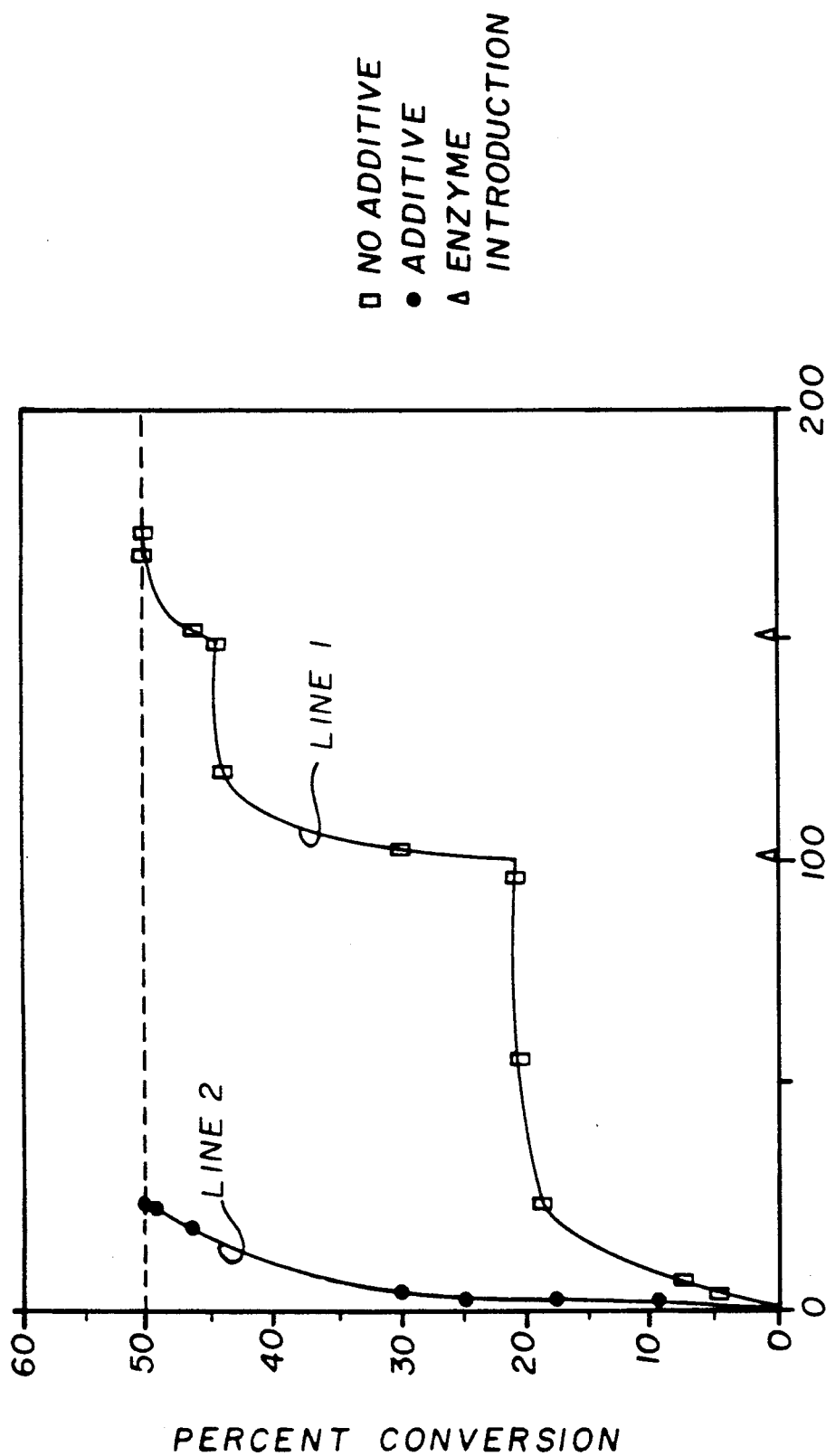
FIG. 1 shows a graphical representation of percent reaction conversion (y-axis) over time (x-axis), as further described in Example I below.

In accordance with the present invention, the achiral acyl donor is an ester. Suitable esters are those represented by formula (A) above where $R^1$ is not a hydroxyl, primary amine or secondary amine. Preferably $R^1$ is defined as the same or different and is selected from the following: a hydrogen atom, a halogen atom (such as, for example, chloro, bromo, fluoro or iodo), a straight or branched $C_1$–$C_{10}$ alkyl group (such as, for example, methyl, ethyl, butyl, t-butyl, propyl, pentyl, methylpentyl, hexyl, isohexyl or decyl), a straight or branched $C_2$–$C_{10}$ alkenyl group (such as, for example, vinyl, allyl, isopropenyl, cis or trans-2-butenyl, 2-methyl-1-propenyl, 1,3-butadienyl, 1,4-pentadienyl or 1,3-pentadienyl), a straight or branched $C_1$–$C_6$ ether (such as, for example, methoxy, ethoxy, n-propoxy, i-propoxy, or sec-butoxy), a straight or branched $C_1$–$C_6$ thioether (such as, for example, methylthio, ethylthio, n-propylthio, isopropylthio, or methylpentylthio), or a tertiary dialkylamino with each $C_1$–$C_6$ alkyl the same or different (such as, for example, dimethylamino, diethylamino, methylethylamino and di-n-propylamino).

More preferably the acyl donor defined by formula (A) is a vinyl ester selected from vinyl acetate, vinyl propionate, vinyl butyrate, isopropenyl acetate or vinyl chloroacetate. For purposes of availability and low cost, most preferably vinyl acetate is employed.

The esters can be produced by methods known to those skilled in the art and some specific examples are available commercially from, for example, Kodak Laboratory and Research Products, Eastman Fine Chemicals, Rochester, N.Y.

The chiral substrate employed in accordance with this invention is a 1,2-diol monosulfonate. Preferably, the 1,2-diol monosulfonates are those represented by formula (B), shown above, wherein:

$R^2$ is a straight or branched, primary or secondary, $C_1$–$C_{10}$ alkyl group (such as, for example, methyl, ethyl, n-butyl, n-propyl, isopropyl, methylpentyl, n-hexyl, isohexyl, n-heptyl, n-octyl and n-decyl); a straight or branched $C_2$–$C_{10}$ alkenyl group (such as, for example, vinyl, allyl, 1-butenyl, isopropenyl, 2-methyl-1-butenyl, 3-methyl-1-butenyl, 1-hexenyl, 1-heptenyl, 1-octenyl and 1-decenyl); or a straight or branched $C_2$–$C_{10}$ alkynyl group (such as, for example, ethynyl, propynyl, 1-butynyl, 3-methyl-1-butynyl, 1-hexynyl, 3-methyl-1-heptynyl, 1-octynyl and 1-decynyl); further, the alkyl, alkenyl and alkynyl groups may be substituted, wherein one or more substituents may be selected from halogen atoms (such as, for example, chloro, bromo, iodo, or fluoro), cyano, $C_1$–$C_5$ butoxy, propoxy, or pentoxy) and $C_1$–$C_5$ alkylthio (such as, methylthio, ethylthio, or propylthio).

Ar represents a substituted or unsubstituted $C_4$–$C_{10}$ aromatic or heteroaromatic group with substituents selected from halogen atoms (such as, for example, chloro, bromo, fluoro or iodo), nitro, or dialkylamino with each $C_1$–$C_3$ alkyl the same or different (such as for example, dimethylamino, methylethylamino, diethylamino or dipropylamino). For example, according to the invention, the —OSO$_2$Ar group of formula (B) may be p-toluenesulfonate, phenylsulfonate, p-bromobenzenesulfonate, 4-chloro-3-nitrobenzenesulfonate, 2,5-dichlorobenzenesulfonate, 5-dimethylamino-1-naphthalenesulfonate, 2,4-dinitrobenzenesulfonate, p-iodobenzenesulfonate, 1-naphthalenesulfonate, 2-naphthalenesulfonate, o-nitrobenzenesulfonate, m-nitrobenzenesulfonate, p-nitrobenzenesulfonate, or 2-thiophenesulfonate.

More preferably, the 1,2-diol monosulfonate is 1,2-propylene glycol monotosylate, 1,2-butylene glycol monotosylate, 1-tosyloxy-2-hydroxy-3-chloropropane or 1-tosyloxy-2-hydroxy-3-butene. Most preferably employed is the 1-tosyloxy-2-hydroxy-3-butene.

The 1,2-diol monosulfonates can be prepared from the corresponding diols by techniques known to those skilled in the art. Many of the diols may be purchased from various suppliers, including Kodak Laboratory and Research Products. An example of a technique is the following reaction sequence for the preparation of 1-tosyloxy-2-hydroxy-3-butene.

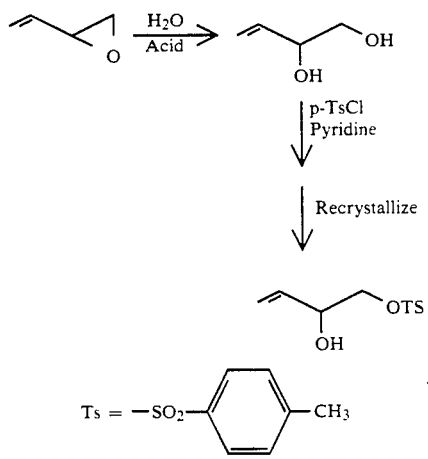

As shown, the route begins by reacting epoxybutadiene ("EpB") with water under neutral conditions or with acid catalysis to afford racemic 1,2-dihydroxy-3-butene. The diol is treated with p-toluenesulfonyl chloride ("p-TsCl") in pyridine at 4° C. to afford the desired monotosylate contaminated with about 10% of the corresponding ditosylate. The monotosylate can be selectively crystallized to afford pure monotosylate in 61% yield.

For the enzymatic acylation reaction, the relative amounts of the acyl donor and the chiral substrate may vary. Preferably employed is a ratio of about 1:1 to about 10:1 of acyl donor to chiral substrate.

According to the invention, the enzyme employed is an enzyme derived from a microorganism or animal organ which has stereoselective activity to asymmetrically esterify the 1,2-diol monosulfonate. Preferably the enzyme is a lipase derived from Pseudomonas sp. Convenient lipases include Lipase AK ™ derived from Pseudomonas sp., Lipase SAM-II ™ derived from *Pseudomonas fluorescens* and Lipase PS-30 ™ derived from *Pseudomonas cepacia* (all of which are commercially available from Amano International Enzyme Company) Mixtures of the enzymes may be employed as well. Generally, the enzymatic enantioselective esterification proceeds using only a small amount of the enzyme. Preferably the enzyme is present in a ratio ranging from about 2.5 mg of enzyme per mmol of the chiral substrate to about 100 mg of enzyme per mmol of the chiral substrate. The enzyme need not be in pure form and may be used in an unpurified state, immobilized or not immobilized. The aforementioned amounts of enzyme are for unpurified, non-immobilized enzymes which are presently preferred because they present the simplest and least expensive option. Lesser amounts of purified materials can be used.

In accordance with the invention, the nonhydroxylic (non-aqueous) organic solvent employed can be selected from any number of compounds that are known to those skilled in the art.

Preferably, for both enzymatic activity and safety reasons, the solvent is an ether (more preferably, diethyl ether, tetrahydrofuran, tert-butyl methyl ether, or dibutyl ether); an aromatic hydrocarbon (more preferably, toluene or xylene); an ester (more preferably, ethyl acetate or vinyl acetate); a ketone (more preferably, acetone or methyl ethyl ketone); or mixtures thereof. Most preferably, the solvent is tert-butyl methyl ether.

In accordance with the invention, the additive is an amine having the general formula $R^3{}_2R^4N$, wherein, $R^3$ may be the same or different and a hydrogen or a straight or branched $C_1$–$C_{20}$ alkyl (such as, for example, methyl, ethyl, propyl, isopropyl, n-butyl, tert-butyl, pentyl, isopentyl, hexyl, isohexyl, heptyl, octyl, nonyl, decyl, tetradecyl and octadecyl); and $R^4$ is a straight or branched $C_1$–$C_{20}$ alkyl (such as, for example, those recited for $R^3$); or an unsubstituted or substituted $C_4$–$C_{20}$ aryl or heteroaryl group. Suitable unsubstituted aryl groups are, for example, phenyl and naphthyl. Suitable substituents on the substituted aryl groups include $C_1$–$C_4$ alkyl groups (such as, for example, methyl, ethyl, propyl or butyl), halogen (such as, for example, chloro, bromo, iodo or fluoro) or $C_1$–$C_4$ alkoxy (such as, for example, methoxy, ethoxy, propoxy or butoxy). Suitable hetero atoms of the heteroaryl include nitrogen, sulfur, or oxygen, with suitable heteroaryls including thienyl, furyl, and pyridyl. Mixtures of the amine additives defined above may also be employed.

More preferably, the additive component is an amine defined as having an in situ formed salt having a pKa of 7 or greater, including triethylamine, trimethylamine, diisopropylethylamine, 4-dimethylaminopyridine, diethylamine, n-butylamine, isopropylamine, tert-butylamine, tripropylamine, mixtures thereof, and the like. Most preferably, the additive is triethylamine or diisopropylethylamine.

According to the invention, the amount of amine additive employed is generally based on the amount of chiral substrate employed. For example, preferably from about 5 to about 1000 mole percent of the additive is employed, based on the chiral substrate. More preferably, from 5 to 100 mole percent is employed, and most preferably from 5 to 25 mole percent is employed.

Although not wishing to be bound by theory, it is believed that the amine additive acts as a scavenger to remove an impurity present in the reaction mixture. It is believed this impurity is a sulfonic acid. The presence of the impurity is believed to increase the reaction acidity, thereby hindering the enantioselectivity and the percent conversion of the esterification. It is believed that small amounts of the impurity may contaminate the substrate and be present initially in the reaction mixture. It is theorized, however, that the majority of the impurity is produced during the enzymatic reaction itself.

The use of the preferred additive, triethylamine, as a co-solvent for enzymatic esterifications is known. The prior art indicates that triethylamine has an accelerating effect when the acyl donor is trichloroethyl acetate (probably due to interactions of the amine with released trichloroethanol) but has no effect when vinyl acetate is the acyl donor, thus teaching away from the present invention. Indeed, 1-phenylethanol, a substrate not possessing the 1,2-diol monosulfonate backbone, shows no change in the rate or enantioselectivity of an enzymatic esterification using Lipase SAM-II.

The order in which the reaction components are contacted is not determinative of the success of the esterification. Generally the contacting may occur in any given order, in either a batch or continuous method. If the 1,2-diol monosulfonate substrate is considered to have a high content of sulfonic acid present as an impurity (which may occur if the substrate has been prepared and stored for a period of time), it is preferred that the amine additive be contacted with the 1,2-diol monosulfonate and solvent prior to employing the other components. Most preferably the 1,2-diol monosulfonate (in solvent) is contacted with the additive and thereafter contacted with the acyl donor and enzyme.

The reaction conditions can be carried out in a manner familiar to those skilled in the art. A pH controlled reaction mixture is not necessary. The process of this invention can be preferably carried out at ambient pressures. Higher and lower pressures can be used, if desired. The reaction time is dependent, at least to some extent, on the amount and activity of the enzyme, on the reactivity of the substrate employed, and the reaction temperature. Generally, a higher reaction temperature increases the rate of the enzymatic esterification. The temperature, however, must not be so high as to inactivate the enzyme. Preferably the temperature falls within the range of about −20° C. to about 100° C., more preferably from 5° C. to 75° C. and most preferably from 15° C. to 60° C. The reaction system is preferably carried out under substantially nonaqueous conditions.

Upon the completion of the reaction, because the enzyme is suspended in organic solvent rather than dissolved in an aqueous reaction condition, the enzyme may be recovered by filtration (and reutilized), and the solvent removed from the filtrate at reduced pressure. This can be accomplished by techniques known to those skilled in the art.

The resulting enantiomerically enriched ester and enantiomerically enriched alcohol reaction products can be separated from each other in various techniques known to those skilled in the art. For example, the mixture can be subjected to silica gel chromatography. In this manner, the enantiomerically enriched compounds are easily separated from each other. Further, in certain circumstances, such as, for example, with the compound mixture S-1-tosyloxy-2-hydroxy-3-butene (S-1) and R-1-tosyloxy-2-acetoxy-3-butene (R-2), the products can be separated by recrystallization wherein the mixture of products present in an organic solvent are brought to a temperature wherein most of the enantiomerically enriched alcohol precipitates, leaving in solution most of the enantiomerically enriched ester. The precipitate is then separated from the solution, thus separating the ester from the alcohol.

Other techniques for recovery of products are described in pending U.S. Ser. No. 660,837 (filed 26FEB91) entitled "Protected Hydroxy Method for Alcohol-Ester Separation" by N. Boaz; U.S. Ser. No. 660,839 (filed 26FEB91) entitled "Alcohol-Ester Separation by reaction with Acetate" by N. Boaz; and U.S. Ser. No. 660,830 (filed 26FEB91) entitled "Alcohol-Ester Separation by Recrystallization" by N. Boaz.

The products thus obtained comprise the 1,2-diol monosulfonate of the general formula

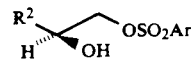

and the antipodal ester of the general formula

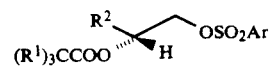

The optical purity of the parent 1,2-diol monosulfonate can be determined by either HPLC using a CHIRALCEL OB column (Diacel Chemical Industries, Ltd.) or by a method analogous to that described in Dale et al., *J Org. Chem.*, 1969, Vol. 33, p. 2543, and can be used to calculate an "E" in accordance with the methods described in (a) Chen, C. S, et al. *J. Am. Chem. Soc.* 1982, 104, p. 7294 or (b) Chen, C,S, et al. *J. Am Chem. Soc.* 1987, 109, p. 2812. A reaction with a high "E" value affording products with high "ee" values is of greater advantage than reactions exhibiting lower enantioselectivity. The more preferred product mixture exhibits an "ee" of greater than 90%±2%. The most preferred product mixture exhibits an "ee" of greater than 96%±2% and an E value of greater than 200.

As demonstrated in the TABLE following the Examples, the invention is advantageous because it provides products exhibiting both an improved reaction conversion percentage ("ee") and higher enantioselectivity ("E").

The present invention is now further illustrated by, but is by no means limited to, the following examples.

1,2-Diol Monosulfonate Preparation

Addition of Water to Epoxybutadiene

Epoxybutadiene (250 g) was added to 800 ml of water, followed by 10 g of an acid resin catalyst. The reaction mixture was stirred at room temperature overnight. The catalysis was removed by filtration, and the filtrate was concentrated at reduced pressure. Distillation of the residue (60°-65° C./1 mm) provided 1,2-dihydroxy-3-butene in 85% yield. $^1$H NMR (CDCl$_3$): 5.9 (m,1H); 5.4–5.2 (m,2H); 4.25 (m, 1H); 3.7 (m, 1H); 3.5 (m, 1H); 2.3 (br s, 1H). IR(CCl$_4$): 3600, 3499 (broad), 2900, 2880 cm$^{-1}$. MS: 87, 70, 57, 42, 31, 29 m/e.

Synthesis of 1-tosyloxy-2-hydroxy-3-butene 1,2-Dihydroxy-3-butene (20.00 g; 0.227 mole; 1.05 equivalent) was dissolved in pyridine (200 ml). The reaction mixture was cooled in an ice bath and p-toluenesulfonyl chloride (p-TsCl) (41.11 g; 0.216 mole) was added in four portions over 30 min. After thorough mixing, the reaction mixture was placed at 4° C. for 18 h, at which time thin layer chromatography (TLC) analysis indicated no p-TsCl. The mixture was concentrated to about half the original volume at reduced pressure from a 40° C. water bath and then diluted with ether (220 ml). The mixture was washed with water (100 ml), ice-cold 3N HCl until the washes remained acidic (2×100 ml), and saturated sodium bicarbonate (100 ml). After drying the organic solution (MgSO$_4$), the solvent was removed to afford 41.73 g of a 91:9 mixture ($^1$H NMR analysis) of the desired compound and the corresponding di-tosylate. The crude product solidified over several days at −20° C. to afford two crops (total 33.33 g; 61%) of the desired compound, 1-tosyloxy-2-hydroxy-3-butene, which was pure by TLC analysis, mp 38°-44° C. $^1$H NMR (300 MHz, CDCl$_3$): 7.800 (2H, d, J=8.25 Hz); 7.356 (2H, d, J=8.19 Hz); 5.751 (1H, ddd, J=5.38, 10.46, 16.55 Hz); 5.378 (1H, br d, J=17.05 Hz); 5.247 (1H, br d, J=10.48 HZ); 4.396 (1H, m); 4.066 (1H, dd, J=3.39, 10.20 Hz); 3.906 (1H, dd, J=7.41, 10.22 Hz); 2.451 (3H, s); 2.276 (1H, d, J=4.50 Hz). IR (KBr, cm$^{-1}$): 3520 (s,b); 1650 (w); 1600 (s); 1350 (s); 1170 (s). Combustion Analysis Calculated—C, 54.53; H, 5.82: N, O. Found —C, 54.84; H, 5.86; N, <0.3.

EXAMPLE 1

Line 2 of FIG. 1 is composed of aliquots removed at specific times and measured for percentage conversion from a run carried out in the following manner:

As prepared in the preparatory scheme shown above, 1-tosyloxy-2-hydroxy-3-butene (1.21 g; 5.0 mmole) was dissolved in the tert-butyl methyl ether (TBME) (5 ml) to form a reaction mixture. The additive triethylamine (Et$_3$N) (70 µl; 0.5 mmole; 0.1 equivalent) was then contacted with the reaction mixture, and the mixture was stirred for 15 min. Vinyl acetate (1.38 ml; 15 mmole; 3 equivalent; supplied by Eastman Fine Chemicals) was then contacted with the reaction mixture, followed by Lipase SAM-II from Pseudomonas Sp. (50 mg). The reaction mixture was stirred at room temperature and aliquots were removed and assayed by $^1$H NMR. The following percent conversion data were collected, with results shown graphically by Line 2 in the FIG. 1. The percent conversion data were: 1 hour, 9%; 2 hours, 17%; 3 hours, 25%; 4 hours, 30%; 16.5 hours, 47%; 20 hours, 49%; and 21 hours, 50%. All data is ±2%.

After 22 h, the reaction mixture was filtered to remove the enzyme and the filtrate was concentrated at reduced pressure to afford the crude mixture of S-1-tosyloxy-2-hydroxy-3-butene (S-1) and R-1-tosyloxy-2-acetoxy-3-butene acetoxy-3-butene (R-2). This mixture was flashchromatographed and eluted with 1:3 ethyl acetate:hexanes to afford S-1 (401 mg; 33%;>99.5% ee) and R-2 (609 mg; 43%; 96.2% ee) as chemically pure samples. The E value was calculated as >308. All non-chiral physical properties of S-1 are as described above.

[α]$_D$ −7.6° (c. 1.030, CH$_3$OH).

The optical purity of S-1 was determined by HPLC analysis on a CHIRALCEL OB column (Diacel Chemical Industries, Ltd.), 10% isopropanol in hexane eluent, flow rate 1 ml/min, λ=254 nm. The optical purity could also be determined (and corroborated) by a method analogous to that described in Dale et al., *J. Org. Chem.*, 1969, Vol. 33, p. 2543.

R-2: $^1$H NMR (300 MHz, CDCl$_3$): 7.786 (2H, d,J=8.26 Hz); 7.355 (2H, d,J=8.03 Hz); 5.710 (1H, ddd, J=6.23, 10.54, 17.05 Hz); 5.396 (1H, m); 5.324 (1H, d,J=16.72 Hz); 5.279 (1H, d,J=10.63 Hz); 4.09 (2H,m); 2.453 (3H, s); 2.017 (3H,s). IR (neat film, cm$^{-1}$): 1740(s); 1645(w); 1600(m); 1360(s); 1175(s). The optical purity of R-2 was determined by initial conversion to R-1 as follows. Compound R-2 (609 mg; 2.14 mmole) was dissolved in methanol (2.5 ml). Concentrated HCl (12 M; 0.18 ml; 2.16-mmole; 1 equivalent) was added and the reaction mixture was stirred overnight at room temperature to completely consume 2 (TLC analysis). The reaction mixture was diluted with ether (25 ml) and washed with saturated aqueous NaHCO$_3$ (2×5 ml). The organic solution was dried (MgSO$_4$) and concentrated to afford R-1 (431 mg; which was analyzed for optical purity using the methods described above for S-1. All non-chiral physical properties of 1 are as described above.

[α]$_D^{20}$ +7.5° (c. 0.825, CH$_3$OH).

The absolute configuration of 1 was determined to be R −(+) by reduction of the olefin of the (+)-alcohol 1 to afford the corresponding (−)-1,2-butanediol monotosylate The compound is known to possess the R-(−) configuration (Hamaguchi, et al., *Agri. Biol. Chem.*, 1986, Vol. 50, p. 1629).

As represented by Line 1 of FIG. 1, a Control was run using the procedure as set forth above using 1-tosyloxy-2-hydroxy-3-butene (2.42 g; 10.0 mmole), vinyl acetate (2.77 ml; 30 mmole; 3 equivalents) and Lipase SAM-II (100 mg), in TB.ME. In this case no amine additive was included in the reaction mixture. Additional enzyme (100 mg each time) was included in the reaction mixture at 101 h and 150 h. Aliquots were measure for percent conversion as follows: 1.5 h, 3.1%; 3 h, 4.7%; 6 h, 7.5%; 24 h, 18.7 %; 56 h, 20.6%; 96 h, 20.7%; 103 h, 29.8%; 119 h, 44.2%; 148 h, 44.4%; 150.5 h, 46%; 151 h, 46.2%; 168 h, 50.1%; and 173 h, The enzyme was removed by filtration and the filtrate was concentrated. A portion of the crude product was flash chromatographed on silica gel to afford R-2, 90% ee, and S-1, 84% ee. These optical purities indicate an "E" value of 50 for the enzymatic esterification.

EXAMPLE 2

A reaction run under identical conditions except using Lipase PS-30 (25 mg) was stopped at 50% convention (42 hours). The lipase was removed by filtration, and the filtrate was concentrated at reduced pressure. The crude product was separated by flash chromatography and eluted with 1:2 ethyl acetate:hexanes and investigation indicated that R-2 possessed 98%±2% "ee" and S-1 possessed 98%±2% "ee". The E value was calculated as 458, as recorded in the TABLE below.

EXAMPLE 3

The procedure of Example 2 was followed with the following changes. The solvent diethoxymethane ["(EtO)$_2$CH$_2$"] was substituted and % conversion was measured at 24 hours to be 44%. At 42 hours the reaction was stopped and % conversion was found to be 50%, with a final "ee" of 84%±2% for S-1 and 94% ±2% for R-2. The "E" value was calculated as 86, as recorded in the TABLE below.

EXAMPLE 4

The procedure of Example 2 was followed with the following changes. The solvent tetrahydrofuran ("THF") was substituted and % conversion was measured at 24 hours to be 41%. At 48 hours the reaction was stopped and % conversion was found to be 34%, as recorded in the TABLE below. The "ee" value was not measured, and the "E" value was not calculated.

EXAMPLE 5

The procedure of Example 2 was followed with the following changes. The solvent ethyl acetate ("EtOAc") was substituted and % conversion was measured at 24 hours to be 30%. At 48 hours the reaction was stopped and % conversion was found to be 27%, as recorded in the TABLE below. The "ee" was not measured, and the "E" value was not calculated.

EXAMPLE 6

The procedure of Example 1 was followed with the following changes. The solvent toluene (PhCH$_3$) was substituted and % conversion was measured at 24 hours to be 48%. At 48 hours the reaction was stopped and % conversion was found to be 50%. The % ee for S-1 was 99%±2% and the % ee for R-2 was 90%±2%. The E value was calculated as 99, as recorded in the TABLE below.

TABLE

Esterification with Triethylamine in Various Solvents

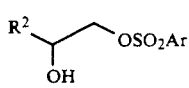

| Solvent | % Conversion at 24 h. | Time Stopped, % Conversion | "ee" % S-1 | "ee" % R-2 | "E" Value |
|---|---|---|---|---|---|
| TBME | 44% | 42 h, 50% | 98% | 98% | 458 |
| (EtO)$_2$CH$_2$ | 41 | 42 h, 50% | 84% | 94% | 86 |
| THF | 30% | 48 h, 34% | * | * | * |
| EtOAc | 27% | 48 h, 27% | * | * | * |
| PhCH$_3$ | 48% | 48 h, 50% | 99% | 90% | 99 |

*no measurements were taken

The invention has been described above with particular reference to preferred embodiments. A skilled practitioner familiar with the above detailed description can make many modifications and substitutions without departing from the scope and spirit of the invention.

That Which is claimed is:

1. A process for the enzymatic esterification of 1,2-diol monosulfonates comprising contacting:
   (a) a vinyl ester selected from the group consisting of vinyl acetate, vinyl propionate, vinyl butyrate, isopropenyl acetate and vinylchloroacetate;
   (b) a 1,2-diol monosulfonate having the formula:

$$R^2 \diagdown \diagup OSO_2Ar \atop OH \qquad (B)$$

wherein
   R$^2$ is a straight or branched, substituted or unsubstituted C$_1$-C$_{10}$ alkyl group, a straight or branched, substituted or unsubstituted C$_2$-C$_{10}$ alkenyl group, or a straight or branched, substituted or unsubstituted C$_2$-C$_{10}$ a alkynyl group, wherein said substituents are selected from the group consisting of halogen, cyano, C$_1$-C$_5$ alkoxy and C$_1$-C$_5$ alkylthio; and Ar represents a substituted or unsubstituted C$_4$-C$_{10}$ aromatic group wherein said substituents are selected from the group consisting of halogen atoms, nitro, or a dialkylamino having alkyl groups with 1 to 3 carbon atoms with each alkyl the same or different;
   (c) an enzyme derived from a microorganism or animal organ which has steroselective activity to asymmetrically esterify said 1,2-diol monosulfonate;
   (d) a nonhydroxylic organic solvent; and
   (e) an amine additive of the general formula R$^3{}_2$R$^4$N,
   wherein
   R$^3$ may be the same or different and is selected from hydrogen or a straight or branched C$_1$-C$_{20}$ alkyl, and
   R$^4$ is a straight or branched C$_1$-C$_{20}$ alkyl;
   to produce a mixture of enantiomerically enriched 1,2-diol monosulfonate and corresponding enantiomerically enriched entipodal ester.

2. The process according to claim 1 wherein said
   (b) is 1,2-propylene glycol monotosylate, 1,2-butylene glycol monotosylate, 1-tosyloxy-2-hydroxy-3-chloropropane or 1-tosyloxy-2-hydroxy-3-butene;
   (c) is a lipase derived from *Pseudomonas sp.;*
   (d) is diethyl ether, tetrahydrofuran, tert-butyl methyl ether, diisopropyl ether, toluene, benzene, ethyl acetate, vinyl acetate, acetone, methyl ethyl ketone or a mixture thereof; and
   (e) is an amine selected from the group consisting of triethylamine, trimethylamine, diisopropylethylamine, diethylamine, n-butylamine, isopropylamine, tert-butylamine, tripropylamine, or a mixture thereof.

3. The process according to claim 2 wherein said
   (c) is a lipase derived from *Pseudomonas fluorescens* or *Pseudomonas cepacia;*
   (d) is tert-butyl methyl ether; and (e) is triethylamine or diisopropylethylamine.

4. The process according to claim 3 wherein said
   (a) is vinyl acetate;
   (b) is 1-tosyloxy-2-hydroxy-3-butene; and
   (c) is Lipase SAM-II or Lipase PS-30

5. The process according to claim 4 wherein:
   (c) is Lipase PS-30; and
   (e) is triethylamine.

6. The process according to claim 4 wherein:
   (c) is Lipase PS-30; and
   (e) is diisopropylethylamine.

7. The process according to claim 1 wherein said amine additive is employed within a range of from about 5 to about 1000 mole percent of said (b).

8. The process according to claim 7 wherein said amine additive is employed within a range of from to 100 mole percent of said (b).

9. The process according to claim 8 wherein said amine additive is employed within a range of from 5 to 25 mole percent of said (b).

10. The process according to claim 9 wherein:
    (a) is vinyl acetate;
    (b) is 1-tosyloxy-2-hydroxy-3-butene;
    (c) is Lipase PS-30;
    (d) is tert-butyl methyl ether; and
    (e) is triethylamine.

11. The process according to claim 9 wherein:
    (a) is vinyl acetate;

(b) is 1-tosyloxy-2-hydroxy-3-butene;
(c) is Lipase PS-30;
(d) is tert-butyl methyl ether; and
(e) is diisopropylethylamine.

12. The process according to claim 1 wherein said (b) is contacted with said (d) and said (e) prior to the introduction of said (a) and (c).

* * * * *